(12) United States Patent
Cresens

(10) Patent No.: US 6,905,245 B2
(45) Date of Patent: Jun. 14, 2005

(54) CONTRAST PHANTOM

(75) Inventor: Marc Cresens, Diest (BE)

(73) Assignee: Agfa-Gevaert, Mortsel (BE)

( * ) Notice: Subject to any disclaimer, the term of this patent is extended or adjusted under 35 U.S.C. 154(b) by 0 days.

(21) Appl. No.: 10/465,084

(22) Filed: Jun. 19, 2003

(65) Prior Publication Data

US 2004/0008821 A1 Jan. 15, 2004

Related U.S. Application Data

(60) Provisional application No. 60/397,011, filed on Jul. 19, 2002.

(30) Foreign Application Priority Data

Jul. 9, 2002 (EP) ............................................ 02100792

(51) Int. Cl.[7] .............................................. G01D 18/00
(52) U.S. Cl. ........................................ 378/207; 378/18
(58) Field of Search ................. 378/18, 207; 250/505.1

(56) References Cited

U.S. PATENT DOCUMENTS

| | | | | | |
|---|---|---|---|---|---|
| 4,400,827 | A | * | 8/1983 | Spears | .......................... 378/207 |
| 5,565,678 | A | * | 10/1996 | Manian | ....................... 378/207 |
| 6,490,336 | B1 | * | 12/2002 | Suess et al. | ................... 378/18 |

FOREIGN PATENT DOCUMENTS

| | | |
|---|---|---|
| DE | 32 48 752 A1 | 7/1984 |
| EP | 0 338 233 A2 | 10/1989 |
| EP | 0 499 975 A1 | 8/1992 |
| WO | WO 94/12855 A1 | 6/1994 |
| WO | WO 200028898 A1 * | 5/2000 ............. A61B/6/00 |

OTHER PUBLICATIONS

Wang et al., "Comprehensive and automated image quality performance measurement of computed radiography systems", Proceedings of SPIE, 2001, vol. 4320, pps. 308–315.*
Search Report for EP 02 10 0792 (Jan. 14, 2003).

* cited by examiner

Primary Examiner—Edward J. Glick
Assistant Examiner—Chin-Cheng Glen Kao
(74) Attorney, Agent, or Firm—Leydig, Voit & Mayer, Ltd.

(57) ABSTRACT

A contrast phantom for assessing the characteristic, exposure-related signal and noise response and dynamic range of an image recording and detection system. The contrast phantom is composed of an absorber medium having a sudden K-edge absorption change of the mass attenuation coefficient for at least one photon energy level in-between the mean and maximum energies of the lowest energy spectrum it is subjected to. The invention further provides a method for assessing the characteristic, exposure-related signal and noise response and dynamic range of an image recording and detection system with the aforementioned contrast phantom.

13 Claims, No Drawings

CONTRAST PHANTOM

This application claims the benefit of U.S. Provisional Patent Application No. 60/397,011 filed Jul. 19, 2002, which is incorporated by reference.

FIELD OF THE INVENTION

The present invention relates to image quality performance measurement of radiography systems. The invention more particularly relates to a phantom for assessing the contrast response of a radiography system.

BACKGROUND OF THE INVENTION

Image quality control of analogue and digital radiographic imaging systems is in most cases performed by analyzing radiographic images made by exposing specific test objects, also called phantoms, to radiation under predefined exposure conditions.

These phantoms may comprise multiple specific test objects in order to enable verification of critical characteristics of a system.

The signal dependent noise, the dynamic range and the corresponding contrast resolution are characteristics of the system that set the image quality.

A single exposure of a test phantom positioned in the optical path between the source of radiation and the radiation detector is sufficient to enable measurement of these characteristics.

A contrast object absorbs part of the radiation to which it is exposed and generates, according to the principles of projection radiography and its semi-transparent nature, a residual image of the phantom on the detector.

By determining the thickness of the radiation attenuating object in each point the amount of attenuation of the radiation is controlled. Indirectly also the local radiation intensity in the shadow image which is generated on the detector is controlled.

Known embodiments of contrast phantoms comprise elongate (one dimensional) wedge-like test objects the thickness of which varies either continuously or step-wise from a minimal to a maximal value.

An example of such a phantom is the phantom denominated by the trade name DIGRAD marketed by the company PEHAMED. This phantom, used for quality control in digital radiography, comprises an elongate, step-wise, copper contrast wedge.

The EUROPHANTOM MAMMO (trade name) of the company PEHAMED which is used for quality control in the field of mammography comprises an aluminum step wedge phantom.

Other embodiments exists wherein the different parts of the contrast phantom are spread over the area of the contrast phantom (two-dimensional).

An example of such an embodiment is described in Proceedings of SPIE vol. 4320 (2001), p. 308–315.

The described contrast phantom is composed of a copper base platen to which on certain locations copper tablets are added and into which on other locations cut-aways are provided so that different thickness levels and a reference level are created.

In this way different locations on the surface of the radiographic detection system can be exposed to mutually very distinct exposure levels by means of a single exposure of the contrast phantom.

The measured signals and noise originating from different zones of analysis in the detected image are mutually compared. Deviations relative to reference values are evaluated for the purpose of periodic control of the intrinsic image quality of the entire radiographic system from source of radiation to image detection.

Irradiation originates from briefly applying by means of a high tension generator an adjustable high tension in between the cathode and the anode material (the target) of an X-ray tube.

The radiation originating in consequence of this—to which a radiographic detection system is exposed—is polychromatic and thus of a heterogeneous kind.

This bundle of photons consists of a large range of components of different wavelengths and corresponding energy levels.

For each field of application, for example mammography, general medical diagnostics, non-destructive material testing, radiotherapy and others a number of application dependent spectra have been defined in terms of anode material, level of applied high tension, type of material and thickness of intrinsic and external filters of radiation that are placed close to the source of radiation. These spectra are also called 'radiation qualities'.

The attenuation of the radiation caused by an irradiated object is mainly caused by absorption of radiation depending on the local thickness of the irradiated material, the type of material the object is composed of and the spectrum of the incident radiation.

Given identical thicknesses, an object made of aluminum absorbs less radiation than a object made of copper.

The X-ray Mass Attenuation Coefficient which is characteristic for the absorbing properties of the material used, increases with augmenting atomic number.

In general this absorption coefficient decreases with increasing photon energy level.

As the energy level of the incident photons increases, the attenuation of the radiation by the object will decrease and the transmission of the object will increase.

This means that radiation of lower energy is relatively more attenuated than radiation of higher energy.

When compared with the incident radiation, not only the intensity of the residual radiation which results from penetration through the object, is attenuated but also the spectrum of the residual radiation is changed as a consequence of the non-uniform attenuation of low- and high energetic photons.

The relative contribution of soft, low-energetic components of the radiation has decreased relative to the contribution of harder, high energetic compounds of radiation.

This perturbation of the energy balance, known as the beam-hardening effect, becomes more explicit as the thickness of the object increases and as the incident radiation has a broader spectrum.

The radiographic system for which the image quality is to be assessed comprises a radiation integrating detector.

This detector is capable of locally measuring the amount of incident radiation and to convert this amount into a radiation image. Such a detector is for example a combination of a radiographic film and an intensifying screen, or a storage phosphor or a solid state radiation detector.

These detectors do not only integrate the incident radiation over time but also integrate the different energy levels that are present in the incident (residual) radiation.

Depending on the detector type used the spectral sensitivity for impinging radiation may vary.

Materials such as copper and aluminum have a Mass Attenuation Coefficient showing a continuous, strongly decreasing behavior with increasing photon energy for the entire spectrum of energies used within the medical diagnostic spectra.

If a contrast phantom with a substantially varying thickness is built from these materials or from materials with a similar behavior in order to obtain a large range of residual radiation intensities at the detector, problems can arise regarding the spectral sensitivity of the contrast object as well as regarding the usability of this contrast object for a wide range of radiation qualities.

Primo, mutual ratios of the different detected residual radiation signals with the reference signal, which corresponds with un-attenuated radiation, will strongly depend on the spectrum of the radiation used when exposing the contrast phantom.

This is caused by the fact that selection of a different energy quality results in the use of a higher or lower energy spectrum of the radiation.

Since the absorption coefficient of the used contrast object is highly sensitive to the selected energy level, large differences of the detected signal ratios will occur for different thickness steps of the wedge when strongly diverging energy qualities are used.

For example a copper step wedge with a thickness of 3.9 mm has the following behavior for different medical spectra used in general diagnostic radiography:

TABLE 1

| spectrum | anode | kVp | filter | unatttenuated/residual ratio |
| --- | --- | --- | --- | --- |
| RQA5 | W | 74 | 2.5 + 21 Al | 300:1 (100% ref.) |
| RQA6 | W | 81 | 2.5 + 26 Al | 127:1 (42%) |
| RQA7 | W | 90 | 2.5 + 30 Al | 52:1 (17%) |
| RQA8 | W | 100 | 2.5 + 34 Al | 27:1 (9%) |
| RQA9 | W | 120 | 2.5 + 40 Al | 12:1 (4%) |

Since a minimal detected signal ratio between the un-attenuated irradiation spectrum and the most attenuated residual spectrum is required in order to obtain a meaningful image quality control, the use of a copper wedge is restricted to application in a very limited spectral range.

In addition component spread and early wear of the X-ray tube, a slightly erroneous setting of the tube voltage or the fact that the ripple of the generator voltage is too high may have as a consequence that a large portion of the anticipated tolerance margins on the nominal signal ratios are already consumed without there being any problem with the performance of the detection system itself.

For a contrast phantom made of copper the sensitivity of the signal detected under an absorption step with a thickness of 3.9 mm for a erroneously set tube voltage of +/−1 kV is

TABLE 2

| spectrum | anode | kVpeak | filter | signal change/ +/−1 kVpeak delta |
| --- | --- | --- | --- | --- |
| RQA5 | W | 74 | 2.5 + 21 mm Al | 13.9% |
| RQA6 | W | 81 | 2.5 + 26 mm Al | 9.1% |
| RQA7 | W | 90 | 2.5 + 30 mm Al | 6.2% |
| RQA8 | W | 100 | 2.5 + 34 mm Al | 3.9% |
| RQA9 | W | 120 | 2.5 + 40 mm Al | 2.4% |

TABLE 2-continued

SUMMARY OF THE INVENTION

The above-mentioned objects are realized by a contrast phantom as set out in claim 1.

Specific embodiments are set out in the dependent claims.

The contrast phantom according to the present invention comprises an absorber medium having a sudden K-edge absorption change of the mass attenuation coefficient for at least one photon energy level in-between the mean and maximum energies of the lowest energy spectrum it is subjected to.

Preferably the K-edge character of the absorber material results from the presence of at least one element chosen from the group of element having an atomic number in the range from 39 to 46 and from 65 to 79. The advantages of this embodiment will be explained below.

In one embodiment the absorbing medium comprises multiple chemical elements, each showing K-edge absorption above a different energy level. These elements are combined to achieve a desired response to radiation spectra they are subjected to, by stacking layers each containing at least one of said elements, or by mixing said elements into a compound material.

Another aspect of this invention relates to a method of assessing the characteristic, exposure-related signal and noise response and dynamic range of a radiation image recording and detection system as set out in the claims.

The method comprises the steps of exposing a contrast phantom as described in claim 1 to an amount of radiation emitted by a source of radiation under pre-defined exposure conditions, thereby generating a radiation image of the contrast phantom, recording said radiation image, detecting the recorded radiation image and generating a digital image representation corresponding with the detected radiation image, evaluating said digital image representation.

DETAILED DESCRIPTION OF THE INVENTION

The invention provides a solution to the restrictions of the use of conventional contrast wedges due to their spectral sensitivity.

The invention furthermore provides that the same phantom with a large contrast range can be applied for image quality control of mutually very different radiation spectra as used within a wide range of applications.

The analysis of the system-specific characteristic exposure response of the detected image signal is also an important topic with regard to controlling the general image quality of a radiographic detection system.

Because of the spectral sensitivity of the detector, it is important that this image quality control is performed under identical spectral exposure conditions.

Characteristic exposure response control is based on a number of images taken at strongly different exposure levels whereby additional exposure monitoring is required due to the shot-to-shot variability of the source of radiation.

The described contrast phantom provides that the spectral deformation of the residual spectra, as described higher with regard to the prior art phantoms, is eliminated to a large extent. Consequentially these residual spectra resemble much more the un-attenuated reference radiation spectrum justifying the use of this phantom for the analysis of the exposure response.

This extension of the functionalities simplifies to a large extent the time-consuming and complex conventional procedure because additional exposures under various exposure conditions with additional exposure monitoring are no longer required.

As described higher, the behavior of the X-ray Mass Attenuation Coefficient of many materials that are used as radiation absorbers in conventional, prior art contrast phantoms decreases monotonously with increasing energy level for all photon energies provided.

This specific energy dependent absorption behavior creates beam hardening or spectral deformation of the residual spectrum towards higher energy levels.

The contribution of high energetic radiation components increases at the expense of a decrease of lower energy components.

The mean photon energy and the associated half value layer of the residual radiation both increase with increasing material thickness.

For a 3.9 mm thick copper absorber these values are represented in the following table for RQA5 and RQA9 spectra:

| Spectrum: | Mean Photon Energy Unattenuated | Mean Photon Energy Residual | Shift |
|---|---|---|---|
| RQA5 | 54.1 keV | 65.8 keV | +11.7 keV |
| RQA9 | 76.9 keV | 95.0 keV | +18.1 keV |
| Spectrum: | Half Value Layer Unattenuated | Half Value Layer Residual | Shift |
| RQA5 | 7.1 mm Al | 10.3 mm Al | +3.2 mm Al |
| RQA9 | 11.5 mm Al | 14.5 mm Al | +3.0 mm Al |

The Mass Attenuation Coefficient is not always decreasing over the whole range.

Due to the K-edge photo-electric effect a considerable increase of the absorption originates for radiation energies higher than the K-edge point which is specific to the absorber element used.

At the K-edge level the incident X-ray photon contains sufficient energy in order to excite an electron at K orbit around the atom's nucleus in a way that it moves to the L orbit. Upon collision the photon disappears completely and the atom becomes ionized.

For aluminum and copper, both having a low atomic number, these K-edge energy levels are:

| Material type | atomic number | K-edge energy level |
|---|---|---|
| Aluminum | 13 | 1.56 keV |
| Copper | 29 | 8.97 keV |

These K-edge energies are situated far below the pre-filtered energy range between 30 keV and 120 keV in which radiation qualities RQA5 and RQA9 for medical general diagnostic radiography are situated.

Beyond the K-edge energy level the Mass Attenuation Coefficient pursues its monotonously decreasing behavior with increasing energy levels.

Similar, abrupt increases of the Mass Attenuation Coefficient also occur at element specific L-edge energy levels for materials with an atomic number above 14 and at element specific M-edge energy levels for materials with atomic number above 33.

Depending on the envisaged radiation quality range for which a contrast phantom is to be developed, this material specific sudden increase of the absorption due to the K-edge can be used to counteract the spectral distortion which originates from beam hardening of the residual spectrum due to increasing the thickness of the absorber or the X-ray tube voltage.

According to the present invention an absorber material type is chosen such that for the lowest energetic radiation spectrum within a given radiation quality range this material has a K-edge energy which is situated between the energy level that corresponds with the mean photon energy and the highest energy level keV-peak of the non-attenuated radiation spectrum.

Such a selection provides that increasing material thickness or X-ray tube voltage will have as a consequence that an increasing portion of the higher photon energies will be removed from the residual spectrum.

This effect compensates for the increase of the mean photon energy and the half value layer thickness so that with a proper selection of the absorber material the energy balance of the residual spectrum is restored.

Spectral variability or fluctuations of the source of radiation in the field which have a stronger influence on the higher energy components in the available spectrum consequentially will have a much smaller impact on the detected signal ratios. This implies an increased spectral immunity of the K-edge balanced contrast phantom according to the present invention.

Consequentially the stability of the detected signal ratios as a function of set radiation spectrum improves within a wide spectral range thereby increasing the applicability of the K-edge balanced contrast phantom for a wide range of radiation qualities.

If only a single material type is selected to fabricate a contrast phantom, then Hafnium with atomic number 72 and M, L and K energies at 2.6, 11.3 and 65.4 kev provides the highest spectral stability for RQA5 to RQA9 general radiography radiation qualities.

The lowest energetic un-attenuated RQA5 spectrum has a Mean Photon Energy at 54.1 keV and a Maximal Photon Energy at 74 keV so that the K edge of Hafnium at 65.4 keV is situated approximately in the center of both.

Using a 1.03 mm thick Hafnium contrast phantom shows the following results:

| spectrum | anode | kVp | filter | unatttenuated/residual ratio |
|---|---|---|---|---|
| RQA5 | W | 74 | 2.5 + 21 Al | 300:1 (100%) |
| RQA6 | W | 81 | 2.5 + 26 Al | 269:1 (90%) |
| RQA7 | W | 90 | 2.5 + 30 Al | 289:1 (96%) |

-continued

| spectrum | anode | kVp | filter | unatttenuated/residual ratio |
|---|---|---|---|---|
| RQA8 | W | 100 | 2.5 + 34 Al | 326:1 (108%) |
| RQA9 | W | 120 | 2.5 + 40 Al | 265:1 (88%) |

The stability of the detected signal ratios varies within the RQA5 to RQA9 spectral range between +8% and −12%.

It will be clear that this result is far better than the contrast stability of a copper contrast phantom with a thickness of 3.9 mm which renders the same contrast for RQA5 but whereby the contrast stability decreases largely for higher energetic spectra so that merely 4% of the initial contrast is left at RQA9.

The residual spectrum of the Hafnium contrast object has a Mean Photon Energy and a Half Value Layer which match better with the corresponding values of the un-attenuated spectrum.

| Spectrum: | Mean Photon Energy Un-attenuated | Mean Photon Energy Residual | Difference |
|---|---|---|---|
| RQA5 | 54.1 keV | 60.6 keV | +6.5 keV |
| RQA6 | 58.6 keV | 60.9 keV | +2.3 keV |
| RQA7 | 63.2 keV | 61.1 keV | −2.1 keV |
| RQA8 | 68.0 keV | 62.0 keV | −6.0 keV |
| RQA9 | 76.9 keV | 78.0 keV | +1.1 keV |

| Spectrum: | Half Value Layer Un-attenuated | Half Value Layer Residual | Difference |
|---|---|---|---|
| RQA5 | 7.10 mm Al | 9.27 mm Al | +2.17 mm Al |
| RQA6 | 8.16 mm Al | 9.35 mm Al | +1.19 mm Al |
| RQA7 | 9.10 mm Al | 9.39 mm Al | +0.29 mm Al |
| RQA8 | 10.13 mm Al | 9.52 mm Al | −0.61 mm Al |
| RQA9 | 11.50 mm Al | 11.70 mm Al | +0.20 mm Al |

The measured differences are clearly much smaller than those measured for a copper phantom having a thickness of 3.9 mm whereby the average shift of the Mean Photon Energy is approximately +14 keV and the average shift of the Half Value layer is approximately +3.1 mm Aluminum.

When selecting a different absorber material from the following list to build the contrast phantom a smaller stability gain for spectra in between RQA5 and RQA9 can be achieved:

| Element: | Symbol: | Atomic number Z: | K-edge [keV] |
|---|---|---|---|
| TERBIUM | Tb | 65 | 52.0 |
| DYPROSIUM | Dy | 66 | 53.8 |
| HOLMIUM | Ho | 67 | 55.6 |
| ERBIUM | Er | 68 | 57.5 |
| THULIUM | Tm | 69 | 59.4 |
| YTTERBIUM | Yb | 70 | 61.3 |
| LUTETIUM | Lu | 71 | 63.3 |
| HAFNIUM | Hf | 72 | 65.4 |
| TANTALUM | Ta | 73 | 67.4 |
| TUNGSTEN | W | 74 | 69.5 |
| RHENIUM | Re | 75 | 71.7 |
| OSMIUM | Os | 76 | 73.9 |
| IRIDIUM | Ir | 77 | 76.1 |
| PLATIMUM | Pt | 78 | 78.4 |
| GOLD | Au | 79 | 80.7 |

If a K-edge stabilized contrast phantom composed of a single material type applicable for the mammographic photon energies situated between 8 keV and 35 keV is envisaged, a material choice from the following list will be beneficial for the spectral stability:

| Element: | Symbol: | Atomic number Z: | K-edge [keV] |
|---|---|---|---|
| YTTRIUM | Y | 39 | 17.0 |
| ZIRCONIUM | Zr | 40 | 18.0 |
| NIOBIUM | Nb | 41 | 19.0 |
| MOLYBDENUM | Mo | 42 | 20.0 |
| TECNETIUM | Te | 43 | 21.0 |
| RUTHENIUM | Ru | 44 | 22.1 |
| RHODIUM | Rh | 45 | 23.2 |
| PALLADIUM | Pd | 46 | 24.4 |

By composing the contrast phantom of two or more materials of different types selected from the materials enumerated in the above tables, it is possible to further improve the spectral stability of the detected signal ratios so that the applicability of the contrast wedge for measuring the characteristic exposure related signal response is even more justified.

Average to high concentrations of one or more of the above-enumerated K-edge materials can be used in combination with other materials in the form of a homogenous alloy or these different materials can be joint as stacked material foils into a spectrally stabilized contrast phantom.

A contrast phantom according to the present invention may have an absorber thickness that varies continuously from one position to an other.

Alternatively the absorber's thickness may vary in a step-wise manner from one position to an other.

The absorber's thickness may change along a given direction or alternatively in two directions.

The variation of the thickness may be achieved by stacking absorber layers with different sizes.

Alternatively absorber thickness variation may be created by shaping a monolithic block.

A contrast phantom may be composed of multiple patches of the same absorber medium and of constant thickness, the patches being spatially distributed.

A highly absorbing shielding material may be arranged around and preferably behind (or before) the absorber to reduce the signal flare component originating from un-attenuated radiation impinging on the detector next to the contrast phantom's absorber material.

A highly absorbing shielding material may also be arranged in-between and preferably behind (or before) the neighboring steps to reduce the cross-talk component originating from the different levels of scattered radiation emitted by surrounding steps.

I claim:

1. A method of assessing a characteristic, exposure-related signal and noise response, and dynamic range of an image recording and detection system comprising the steps of
    exposing a contrast phantom to an amount of radiation selected from a plurality of radiation energy spectra emitted by a source of radiation under pre-defined exposure conditions, thereby generating a radiation image of said contrast phantom,
    recording said radiation image,
    detecting the recorded radiation image and generating a digital image representation corresponding with the detected radiation image,
    evaluating said digital image representation, wherein contrast phantom shows a sudden k-edge absorption change of the mass attenuation coefficient for at least one X-ray energy level in between mean and maximum energies of the lowest energy spectrum it is subjected to.

2. A method according to claim 1, wherein the contrast phantom comprises an absorber medium having a sudden K-edge absorption change of the mass attenuation coefficient for at least one photon energy level in between the mean and maximum energies of the lowest energy spectrum it is subjected to.

3. A method according to claim 2, wherein the K-edge character of the absorber medium results from the presence of at least one element chosen from the group of elements having an atomic number in the range from 39 to 46 and from 65 to 79.

4. A method according to claim 2, wherein said absorber medium is HAFNIUM.

5. A method according to claim 2, wherein said absorbing medium is TANTALUM.

6. A method according to claim 2, wherein said absorbing medium comprises multiple chemical elements, each showing K-edge absorption above a different energy level, said elements being combined to achieve a desired response to radiation spectra it is subjected to, by stacking layers each containing at least one of said elements, or by mixing said elements into a compound material.

7. A method according to claim 2, wherein the absorber thickness varies continuously from one position to another.

8. A method according to claim 7, wherein the variation of the thickness of the absorber medium is created by shaping a monolithic block.

9. A method according to claim 2, wherein the thickness of the absorber medium varies in a step-wise manner from one position to another.

10. A method according to claim 9, wherein the variation of the thickness is achieved by stacking absorber layers with different sizes.

11. A method according to claim 9, wherein the constant phantom comprises multiple patches of the same absorber medium and is of constant thickness, said patches being spatially distributed.

12. A method according to claim 2, wherein the thickness of the absorber medium changes along a given direction.

13. A method according to claim 2, wherein the thickness of the absorber medium changes in two directions.

* * * * *